(12) United States Patent
Ramana et al.

(10) Patent No.: US 6,541,269 B1
(45) Date of Patent: Apr. 1, 2003

(54) COLORIMETRIC TEST STRIPS

(75) Inventors: Vasili V. Ramana, Rock Hill, SC (US);
Kami R. Yamuna, Rock Hill, SC (US);
Ivars Jaunakais, Rock Hill, SC (US)

(73) Assignee: Industrial Test Systems, Inc., Rock Hill, SC (US)

( * ) Notice: Subject to any disclaimer, the term of this patent is extended or adjusted under 35 U.S.C. 154(b) by 0 days.

(21) Appl. No.: 10/100,125

(22) Filed: Mar. 19, 2002

Related U.S. Application Data

(63) Continuation of application No. 08/540,413, filed on Oct. 6, 1995, now abandoned, which is a continuation of application No. 08/253,925, filed on Jun. 3, 1994, now abandoned.

(51) Int. Cl.⁷ .............................................. G01N 21/77
(52) U.S. Cl. ........................ 436/165; 436/165; 422/56; 422/58
(58) Field of Search ................. 436/165, 169; 422/56–58

(56) References Cited

U.S. PATENT DOCUMENTS

| | | | |
|---|---|---|---|
| 3,006,735 A | 10/1961 | Jordan | 436/79 |
| 3,453,180 A | 7/1969 | Fraser, Jr. et al. | 435/14 |
| 3,510,263 A | 5/1970 | Hach | 436/163 |
| 3,802,842 A | 4/1974 | Lange et al. | 436/169 |
| 4,092,115 A | 5/1978 | Rupe | 436/125 |
| 4,303,409 A | 12/1981 | Ogawa et al. | 436/93 |
| 4,587,102 A | 5/1986 | Nagatomo et al. | 422/56 |
| 4,837,373 A | * 6/1989 | Gunkel et al. | 422/56 |
| 4,904,605 A | 2/1990 | O'Brien | 436/169 |
| 5,187,100 A | 2/1993 | Matzinger | 436/16 |
| 5,491,094 A | 2/1996 | Ramana et al. | 436/125 |
| 5,498,547 A | * 3/1996 | Blake et al. | 436/111 |
| 5,620,658 A | * 4/1997 | Jaunakais | 422/58 |

OTHER PUBLICATIONS

Ultra + Blood Glucose Monitoring Test Strips, Directions for Use, Apr. 1992.
Environmental Test Systems, Inc., Pool and Spa Test Strips Label, 1994 2000 General Properties pf Filter Papers, Whatman 2000 Product Guide (2000).
Schliecher & Schuell Non–Wovens Specifications (1995).
Schliecher & Schuell Media Specifications, date unknown.

* cited by examiner

Primary Examiner—Maureen M. Wallenhorst
(74) Attorney, Agent, or Firm—Timothy R. Kroboth

(57) ABSTRACT

A method and calorimetric test strip for determining analyte concentration are provided. The test strip includes an aperture exposing a face of an calorimetric indicator-bearing carrier. Sensitivity is enhanced by flowing contact of the liquid to be analyzed, through the carrier and with the indicator.

16 Claims, 1 Drawing Sheet

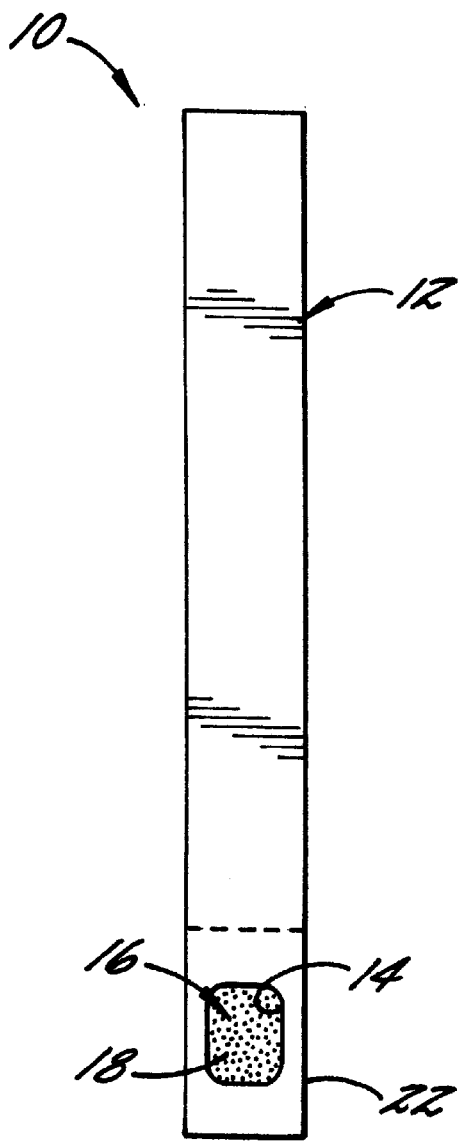
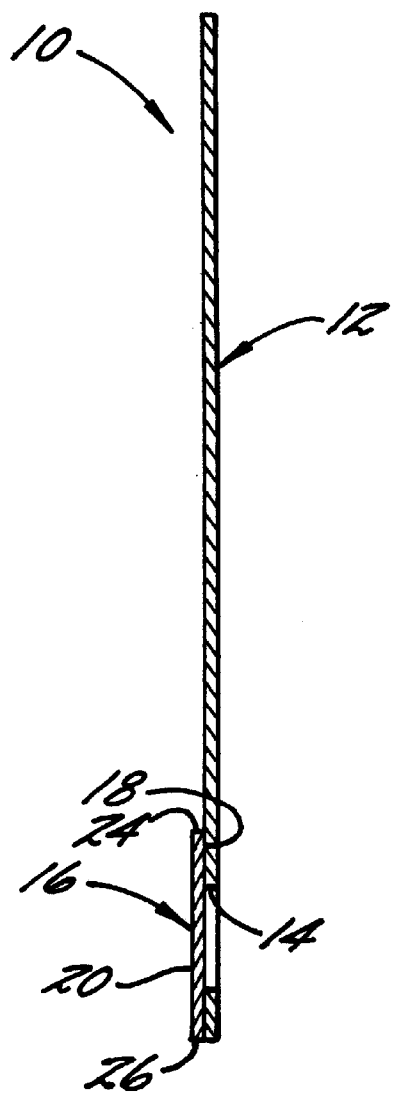
Fig. 1.
Fig. 2.

COLORIMETRIC TEST STRIPS

This application is a continuation of application Ser. No. 08/540,413, filed on Oct. 6, 1995, now abandoned, which is a continuation of application Ser. No. 08/253,925, filed on Jun. 3, 1994, now abandoned.

FIELD OF THE INVENTION

This invention relates to calorimetric test strips.

BACKGROUND OF THE INVENTION

Colorimetric test strips or reagent strips are well known. Areas of use include tap water quality testing, industrial and environmental testing, pool and spa testing, lake and stream testing, aquarium testing and other types of water testing. Test strips also have medical applications including blood and urine analysis. Simple, quick and accurate testing is advantageous, and a test strip must have the necessary detection capability.

Test strips typically include an absorptive carrier bearing a calorimetric indicator, for instance, absorptive paper impregnated with an indicator, or a support having affixed thereto a porous, absorbent carrier bearing an indicator. Exemplary are the test strips of U.S. Pat. Nos. 3,006,735 and 4,904,605. As described therein, the strip may be used by a quick-dipping technique or, in the case of the strip of the '605 patent, may be moved back and forth vigorously for thirty seconds.

A modified reagent strip including a porous matrix bearing reagents and having exposed opposite faces, is illustrated by U.S. Pat. No. 5,187,100. A blood sample is placed in an aperture that exposes a face of the matrix, and the blood seeps from capillary effect to the opposite face. Glucose in the blood reacts with the reagents which include enzymes. In a similar strip, the matrix is disposed between support members provided with apertures generally in line with each other.

Also known as exemplified by U.S. Pat. No. 4,092,115 is a test strip including a wick member enclosed in a fluid impervious sheath, and including an aperture exposing a portion of the wick member bearing colorimetric indicator. The strip is dipped into a sample and held therein until the wick member absorbs the desired amount of fluid or becomes saturated. A drawback of this type of device is non-uniform color development. Additionally, use of the reagents described therein, produces non-stable color. Also, as shown by U.S. Pat. No. 3,510,263, the faces of a chromatographic test strip may be coated with a water repellent material, and the edges may be uncoated.

There continues to be a need for a colorimetric test strip and methodology of enhanced sensitivity. Uniform color development would be advantageous. Moreover, a broad range of sensitivity would be beneficial. It would be also advantageous for the test strip to be economical to manufacture.

SUMMARY OF THE INVENTION

In accordance with the present invention, an improved colorimetric test strip and method useful for a variety of analytes, are provided. The test strip includes a fluid-permeable carrier bearing a calorimetric indicator. The indicator selected, depends upon the analyte of interest. The carrier is beneficially attached to a support advantageously provided with an aperture exposing a face of the carrier. Beneficially, the opposite face of the fluid-permeable carrier is exposed or uncovered, permitting fluid flow through the aperture and carrier.

During an analysis, the carrier may be contacted with a liquid to be analyzed, and the liquid caused to flow through the fluid-permeable carrier and to contact the calorimetric indicator over a selected period of time. When the carrier is dipped into the liquid, a gentle swirling action is beneficially used to cause the liquid to be in flowing contact with the indicator. After the selected contact time, the carrier is evaluated for detectable color change advantageously by viewing the area of the carrier defined by the aperture.

A benefit of the present invention is uniform color development. The color may be compared to a color chart to determine the analyte concentration. The color intensity that develops, increases as the concentration of the analyte in the sample increases and can be quantitatively determined with reproducible sensitivity and accuracy.

In the drawing and in detailed description of the invention that follows, there is essentially shown and described only a preferred embodiment of this invention, simply by way of illustration of the best mode contemplated of carrying out this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

FIG. 1 is a perspective view of a test strip in accordance with the present invention; and FIG. 2 is a longitudinal sectional view of the test strip of FIG. 1.

DETAILED DESCRIPTION OF THE INVENTION

As will become understood, the present invention provides improvements in sensitivity of 30-fold and more. Accordingly, the present invention is beneficially useful for analysis of a sample containing as little as 0.05 ppm (0.05 mg/L) analyte. Moreover, a visually uniform color change is observable, with the change being proportional to the concentration of the analyte present and the sample contact time. Benefits include that the test device can measure a broad concentration range by varying the contact time. The invention has medical applications such as urine analysis, as well as non-medical applications. A variety of analytes such as copper, iron, free chlorine and total chlorine, may be analyzed in water-based samples.

Referring to the drawing, a colorimetric test strip or reagent strip 10 in accordance with the present invention, is shown. Strip 10 conveniently includes a support or handle member 12, which is typically a rigid plastic strip or stick. A conventional thickness of the support ranges from about 0.008 to 0.020 inches; however, as will be understood, the thickness may vary from this range. It will be understood that the term "strip" as used herein, is not limited to an elongated strip-like shape, for the reason that such a shape is immaterial to the invention.

Various thermoplastic materials may be used as the support, with preferred materials for economy being available at low cost, for instance, recycled resins. Suitably, the support may be made of for example, PVC or polyester. It is generally preferable that the support is white, but as can be readily appreciated, the support may be colored by for instance, treatment with a dye.

Beneficially, at or near an end 22 of the support, an aperture 14 is provided. The aperture may have a variety of shapes such as oval, round, square, rectangular, star, triangular and diamond. Advantageously, the aperture is limited in size to effectively direct fluid flow through a limited area. Typically, the aperture, when round, will be about ⅛" to ½" in diameter.

Attached to the support and located so as to be exposed by the aperture, is a fluid-permeable carrier 16. Fluid-permeability of the carrier and exposure of the carrier beneficially provide for fluid flow through the aperture and the carrier. The carrier will typically have a thickness of about 0.002 to 0.02 inch, with a thickness of about 0.01 inch generally being particularly suitable.

Conveniently, a face 18 of the fluid-permeable carrier may be in direct contact with the support. To enable fluid flow through the carrier, a face 20 of the carrier advantageously directly opposite to the exposed portion (as defined by aperture 14) of face 18, is beneficially exposed or uncovered. Suitably, the sides (all not shown) of the carrier may also be exposed or uncovered, as shown for top and bottom sides 24, 26 of the carrier. For purposes of this description, by "face" is meant a principal or wide surface of the permeable carrier, as opposed to a narrow surface or side of the carrier such as the edge of U.S. Pat. No. 3,510,263.

As may be readily appreciated, a suitable permeable carrier maintains its structural integrity during use. Materials useful as permeable carriers are well known, and include polyamide, nitrocellulose and polyester filtration materials. A useful carrier assists in retention of colorimetric chemicals and in low level sensitivity, and in this regard, a filtration material commercially available as Schleicher and Schuell 8-S filter paper, is particularly useful. Other useful carriers include woven or matted glass fiber, nonwoven and woven fabrics, and other filter papers. It will be understood that other permeable matrices that maintain structural integrity in use, may be useful.

Deposited on the carrier is a colorimetric indicator (represented in FIG. 1 as dots), which may be one or more indicators. The colorimetric indicator may be organic or inorganic, but in any event will be suitable for the analyte to be measured. In the case of a water sample, it is beneficial for the indicator and other calorimetric test additives to be insoluble in or not readily soluble in water, to prevent leaching from the carrier especially during an extended sample contact time. Accordingly, the indicator and other test additives may advantageously be substantially insoluble in the liquid being analyzed.

Indicators useful for evaluating chlorine include benzidine-type chromogens, diaminothiobenzo-phenone-type chromogens, and azine compounds such as syringaldazine and vanillinazine. Indicators useful for evaluating iron include 2,4,6-tri(2-pyridyl)-1,3,5-triazine (TPTZ), and useful for evaluating copper include 5-(4-dimethylaminobenzylidene)rhodanine. Other suitable indicators may be selected.

Benzidine indicators especially useful for evaluating free chlorine, include the 3,3',5,5'-tetraalkylbenzidines, wherein alkyl is C1–C3 alkyl, in particular methyl and ethyl, and 3,3',5,5'-tetramethyl-benzidine (TMB) is particularly preferred. Other benzidines within the foregoing formula, include 3,3'-dimethyl, 5,5'-diethyl benzidine and 3,3',5,5'-tetraethylbenzidine. As may be understood, the four alkyl groups may be the same or different. To prevent leaching from the carrier in a water-based sample, the free base form is typically preferred.

Diaminothiobenzophenone indicators especially useful for evaluating total chlorine, include the 4,4'-bis(dialkylamino)thiobenzophenones, wherein alkyl is C1–C3 alkyl, in particular methyl and ethyl, and 4,4'-bis(dimethylamino)thiobenzophenone is particularly preferred. Other thiobenzophenones within the foregoing formula include 4,4'-bis(diethylamino)thiobenzophenone. As may be understood, the four alkyl groups may be the same or different.

Deposition of colorimetric indicator onto the carrier is most desirably for economical reasons by a single step; however, a multi-step procedure may be used. In a single step procedure involving more than one solution, the solutions are combined and the carrier is contacted with the combined solution. In a multi-step procedure, the solutions are not combined, and the carrier member is typically dried after contact with each solution. For purposes of this description, the term "solution" includes a true solution, a turbid solution, and a suspension.

Deposition of calorimetric indicator may be accomplished in any of several ways. A suitable way is to pass the carrier through an impregnation bath containing the indicator so that the carrier becomes saturated with the impregnation solution. The carrier may be then dried at room temperature or at an elevated temperature such as about 120° to 180° F. However, any technique may be used that deposits the calorimetric test chemicals on and/or impregnates the carrier. If beneficial, the carrier may be multi-phasic.

Advantageously, the concentration of the calorimetric indicator in an impregnation solution and the residence time of the carrier in the solution are selected to ensure deposition of the appropriate amount of the indicator. Generally speaking, the residence time is usually not significant, and may vary from several seconds to several minutes, typically about two to thirty seconds, depending upon the calorimetric indicator and carrier. Typically, from about 0.05 to 2 mg, preferably about 1 to 1.5 mg, of colorimetric indicator will be deposited per test strip, for a strip of about 0.01" thickness, ⅜" width and ½" height, but in any case, the amount deposited will be sufficient for colorimetric determination of the analyte of interest. In the case of the benzidines, it has been found that stable color development is suitably provided for, by using a solution level of about 0.5 wt. %.

Advantageously, the indicator solution may include a wetting agent for improved wetting of the carrier and other beneficial effects including enhancement of color development. Illustrative is a polyethoxylated fatty alcohol, nonionic surfactant commercially available from GAF under the name Emulphor ON870, which is advantageous. Other suitable wetting agents, with suitability depending upon the carrier selected, include an anionic surfactant such as dioctyl sodium sulfosuccinate.

In addition, the solution containing the indicator, may beneficially include a stabilizing agent for preventing undesired degradation of the indicator. Beneficially, like the wetting agent, this agent is substantially insoluble in the liquid to be analyzed, to prevent leaching from the carrier. Illustrative is an interpolymer of a lower alkylvinyl ether, and a lower alkyl-substituted or unsubstituted, 1,2-ethylenedicarboxylic acid lower alkyl monoester. By "lower alkyl" is meant methyl, ethyl and propyl. Suitably, the interpolymer is an equimolar reaction product. Particularly useful is an interpolymer of methylvinyl ether and maleic acid isopropyl monoester, which is commercially available from GAF Corporation as Gantrez ES-335 I. Incorporated herein by reference is disclosure relating to the related anhydride and set forth in U.S. Pat. No. 3,453,180.

Also beneficial may be one or more organic or inorganic buffers for providing the appropriate pH. For free chlorine, a carrier pH effective to prevent chloramine interference is advantageous. When TMB is the indicator, a preferable carrier pH ranges from about 6.2 to 7, for free chlorine analysis.

Exemplary useful buffers include phosphate buffers such as monosodium phosphate (MSP), disodium phosphate (DSP) and trisodium phosphate (TSP), and organic buffers such as N-[2-hydroxyethyl]piperazine-N'-[2-hydroxypropanesulfonic acid] known as HEPPSO, 3-[N-tris(hydroxymethyl)methylamino], [2-hydroxypropanesulfonic acid] known as TAPS, and N,N-bis[2-hydroxyethyl]glycine known as BICINE.

In addition, it may be beneficial to deposit on the carrier an additive for fixing the indicator on the carrier. Illustrative is a polymeric film former such as polyvinyl pyrrolidone. Particularly useful is polyvinyl pyrrolidone having an average molecular weight of 60,000 and commercially available as PVP K-60 Solution (PVP-60).

If necessary or desired, one or more coagents or agents otherwise assisting in the analysis of interest, may also be deposited on the carrier. As will be understood, this type additive and the appropriate amount thereof will vary depending upon the calorimetric indicator and other considerations. However, generally speaking, it is not contemplated that cupric salt, peroxide, oxidase or other enzymatic coagent will be used. As a result, the carrier will typically be free of any such coagent.

Attachment of the carrier to the support may be accomplished in a variety of ways. A suitable way is by use of a double-faced adhesive material. The adhesive material is layered down onto the support with tape liner on top. The aperture may then be punched out, the tape liner removed, and the carrier affixed by the adhesive surrounding the aperture. Other suitable methods for attaching the carrier to the support include heat sealing and ultrasonic sealing. Still another method is to dispose the carrier between two supports provided with apertures generally in line with each other. It will be understood that the method of attachment is not limited to the methods just described.

Advantageously, the time of contact of the liquid being tested, with the indicator, is selected to ensure the appropriate sensitivity. As will be understood from the following examples, the time may vary considerably depending upon the calorimetric indicator, the analyte of interest, and the sensitivity of interest. Typically, the time will vary from about 1 second to 90 seconds. While not in any way being bound by this theory, it seems that a relatively greater contact time enables the aperture to direct or channel relatively more fluid flow through a limited area and thereby provides relatively more contact of colorimetric reagent with the analyte of interest.

Typically, the carrier is dipped into the liquid to be analyzed. When a dip-and-read technique is sufficient for the sensitivity needed, the carrier is immediately withdrawn. However, when enhanced contact is desirable, a gentle swirling action is beneficially used to cause the liquid to be in flowing contact with the indicator, after which the carrier is withdrawn from the liquid. A vigorous action as employed is U.S. Pat. No. 4,904,605, is typically unnecessary and may even be detrimental. Accordingly, by the term "gentle action" is meant mild or moderate action. In accordance with the present invention, the test strip may be moved within the liquid in a variety of useful ways, for instance, back and forth or using rotational motion, to cause flow through the carrier. As may be understood, rigidity of the support assists effective movement of the carrier within the liquid. Motion of the carrier within the liquid is beneficially lateral, rather than vertical. In any event, whether the action is gentle or vigorous, and regardless of the type of effective motion used, the present invention is especially characterized by uniformity of color development within the area defined by the aperture.

It is, of course, not necessary to dip the carrier in the liquid; for instance, the carrier may be contacted with flowing tap water. Regardless whether the carrier is dipped or not, an extended sample contact time for purposes of this invention, is about five seconds or more, with about ten seconds or more frequently being desirable, and with about forty seconds or more, even ninety seconds, being highly useful in certain instances.

After the selected contact time, the carrier is evaluated for detectable color change. Beneficially, with respect to the embodiment of the drawing, color is evaluated from the aperture side of strip 10. By comparison, the color on opposite face 20 may be non-uniform outside the area defined by aperture 14. When the carrier is disposed between supports provided with apertures generally in line with each other, the color may be evaluated by viewing the color within either aperture.

Typically, the liquid to be analyzed is water-based. In an illustrative medical application of a water-based sample, urine may be analyzed and a colorimetric indicator suitable for the analyte of interest, is used. If desired, lead or iron may be analyzed. The following examples illustrate an application of the present invention to water-based samples, in testing for free chlorine. In these examples and throughout this description, all parts and percentages are weight percent unless otherwise specified.

EXAMPLE 1

The following solutions are prepared.

| Solution A | |
|---|---|
| Tetramethylbenzidine | 0.6 g |
| Acetone (purified) | 10.0 g |
| Ethanol (absolute) | 50.0 g |
| Gantrez ES-335 I | 4.0 g |
| 10% Emulphor ON870 in ethanol | 2.0 g |
| Solution B | |
| Water | 60.0 g |
| Sodium diphosphate | 1.0 g |

While stirring solution A, solution B is added slowly to solution A. Thereafter, filter paper commercially available as Schleicher and Schuell 8-S filter paper, is dipped into the resulting solution for several seconds and dried. The impregnated, dried filter paper is disposed over a ¼" diameter aperture in a rigid, white polyester support and attached to the support by heat sealing. The support is 0.008" thick, ⅜" wide and 2½" long. Based upon an accelerated stability study at an elevated temperature of 55° C., the resulting test strip is expected to have at least 2 years stability at room temperatures when stored with a desiccant.

Chlorine standards from sodium hypochlorite are prepared with levels of 0.05, 0.1, 0.2, 0.5, 1.0, 2.0, 5.0, 10.0, and 25 ppm. The chlorine levels are confirmed using a reference analytical test method.

Dip times of 1, 10, 30 and 90 seconds are used during which time (except for the 1 second dip) the strips are constantly and gently swirled in the chlorine standards to effect liquid flow through the filter paper carrier. After the selected dip time, the strip is removed from contact with the liquid and visually inspected for color change.

Color uniformity on the filter paper is observed in the area defined by the aperture. The color is observed to be stable for several minutes, the only color change

TABLE 1

| Free Chlorine level PPM | Color found after dip time (in seconds) | | | |
|---|---|---|---|---|
| | 1 | 10 | 30 | 90 |
| 0 | White | White | White | White |
| 0.05 | White | White | White | Very Lt Blue |
| 0.1 | White | White | Very Lt Blue | very lt Blue |
| 0.2 | White | Very Lt Blue | Very Lt Blue | Lt Blue |
| 0.5 | White | Lt Blue | Lt Blue | Blue |
| 1.0 | Very Lt Blue | Blue | Blue | Dk Blue |
| 2.0 | Lt Blue | Dk Blue | Very DK Blue | Very Dk Blue |
| 5.0 | Blue | Very Dk Blue | Very Dk Blue | Very Dk Blue |
| 10 | Dk Blue | Very Dk Blue | Very Dk Blue | Very Dk Blue |
| 25 | Very Dk Blue | Very Dk Blue | Very Dk Blue | Very Dk Blue |

TABLE 2

| Free Chlorine PPM | Color Found After Dip Times (in seconds) | | | |
|---|---|---|---|---|
| | 1 | 10 | 30 | 60 |
| 0 | White | White | White | White |
| 0.2 | White | White | White | V. Lt. Lavender |
| 0.5 | White | White | V. Lt Lav. | Lt. Lavender |
| 1.0 | V. Lt. Lav. | V. Lt Lav. | Lt. Lav. | Lavender |
| 2.0 | Lt. Lavender | Lt. Lav. | Dk. Lav. | Purple |
| 5.0 | Lavender | Lavender | Dk. Lav. | Dk. Purple |
| 10.0 | Purple | Purple | Purple | Dk. Purple | being due to drying of the filter paper. The relationship of free chlorine level and dip time to the color developed, is shown in Table 1.

As indicated in Table 1, low level sensitivity is enhanced as dip time is increased. Thus, sensitivity of free chlorine levels less than 1 ppm is realized using a dip time of about 5 to 10 seconds or more, with sensitivity of even about 0.05 ppm being obtained using a dip time of about 90 seconds. Compared to conventional chlorine test strips having a sensitivity of about 1 ppm, the present invention provides an about 20-fold improvement. While not in any way being bound by this theory, it seems that the aperture functions to direct fluid flow through a limited area and thereby provides enhanced contact of calorimetric reagent with free chlorine. Also shown in Table 1 is a broad detection range of 0.05 to 25 ppm free chlorine, with visually distinctive color development at intermediate levels, using more than one dip time.

In swimming pools, a free chlorine level of about 1 ppm is typically considered to be ideal, with a range of about 0.4 to 2 ppm being usually acceptable. A dip time of about ten seconds beneficially distinguishes levels ranging from about 0.2 to 3 ppm. When superchlorinating, the target free chlorine level is approximately 8 to 10 ppm. A dip time of about 1 second would be advantageously used to check the level after superchlorinating.

In tap water, a free chlorine level of about 0.2 ppm is generally considered to be normal. Therefore, as shown in Table 1, a dip time of about 30 seconds beneficially provides the needed sensitivity. Accordingly, the dip time selected, depends upon the free chlorine level of interest.

EXAMPLE 2

The following solution is prepared:

| | |
|---|---|
| syringaldazine | 0.1 g |
| vanillinazine | 0.1 g |
| Ethanol | 75.0 g |
| Phosphate buffer (0.1 M) | 15.0 g |

Schleicher and Schuell 8-S filter paper is dipped into the solution for several seconds and dried. The impregnated, dried filter paper is disposed over a ¼", star-shaped aperture in a rigid, white PVC support and attached to the support by ultrasonic sealing. The support is 0.008" thick, ⅜" wide and 3" long.

Free chlorine standards are prepared with levels of 0.2, 0.5, 1.0, 2.0, 5.0 and 10 ppm. The chlorine levels are confirmed using a reference analytical test method.

Dip times of 1, 10, 30 and 60 seconds are used during which time (except for the 1 second dip) the strips are constantly and gently swirled in the chlorine standards to effect liquid flow through the filter paper carrier. After the selected dip time, the strip is removed from contact with the liquid and visually inspected for color change.

Uniformity of color on the carrier is observed in the area defined by the aperture. However, the color is observed to fade and therefore color match must be done immediately. The relationship of chlorine level and dip time to the color developed, is shown in Table 2.

As indicated in Table 2, low level sensitivity is enhanced as dip time is increased. Thus, sensitivity of free chlorine levels less than 1 ppm is realized using a dip time of about 30 seconds or more, with sensitivity of about 0.2 ppm being obtained using a dip time of about 60 seconds. Also shown in Table 2 is a broad detection range of 0.2 to 10 ppm chlorine, with visually distinctive color development at intermediate levels, using more than one dip time. Compared to conventional chlorine test strips using the same colorimetric reagents and having a sensitivity of about 1 ppm, the present invention provides an about 5-fold improvement.

The present invention may be carried out with various modifications without departing from the spirit or essential attributes thereof, and accordingly, reference should be made to the appended claims, rather than to the foregoing specification as indicating the scope of the invention.

What is claimed is:

1. A calorimetric analysis method using an apertured test strip comprising a support provided with an aperture therein and a fluid-permeable, calorimetric indicator-bearing carrier having a first face and a second face opposite said first face, wherein said first face of said carrier is attached to said support at the location of said aperture to expose said first face, and wherein said second face of said carrier is uncovered to permit fluid flow through said carrier, said analysis method comprising:

immersing said aperture of said test strip in a liquid to be analyzed and moving said aperture within said liquid using a motion of said test strip selected from the group consisting of a back-and-forth motion and a swirling motion, to direct fluid flow for 10 seconds or more through said aperture and into flowing contact with said indicator on said fluid-permeable carrier, wherein rigidity of said support during said moving step assists effective movement of said aperture, whereby uniformity of color development of said carrier occurs within said aperture, and thereafter withdrawing said carrier from said liquid and evaluating the area of said carrier within said aperture, for a detectable color change.

2. The method of claim 1, wherein said motion is a back-and-forth motion.

3. The method of claim 1, wherein said motion is a gentle back-and-forth motion.

4. The method of claim 1, wherein said motion is a gentle swirling motion.

5. The method of claim 1, wherein said indicator is suitable for analysis of pool or spa or potable water.

6. The method of claim 1, wherein said indicator is suitable for free chlorine analysis.

7. The method of claim 6, wherein said motion is a gentle back-and-forth motion and said liquid is potable water.

8. The method of claim 1, wherein said indicator is suitable for analyte analysis of urine.

9. The method of claim 1, wherein said fluid-directing movement of said aperture is for 30 seconds or more.

10. The method of claim 1, wherein said fluid-directing movement of said aperture is for about 40 seconds or more.

11. The method of claim 1, wherein said support is a plastic support.

12. The method of claim 1, wherein said aperture is completely bounded by said support.

13. The method of claim 1, wherein during the step of moving said test strip, the liquid flows through said first face of said carrier and said positely disposed second face of said carrier.

14. The method of claim 13, wherein said aperture exposes a portion of said first face of said carrier, and wherein said carrier further comprises an uncovered side.

15. The method of claim 1, wherein said indicator is substantially insoluble in said liquid.

16. The method of claim 1, wherein said carrier comprises an additive deposited thereon for fixing said indicator on said carrier, and said additive is a polyvinylpyrollidone polymer.

* * * * *

UNITED STATES PATENT AND TRADEMARK OFFICE
CERTIFICATE OF CORRECTION

PATENT NO.     : 6,541,269 B1
DATED          : April 1, 2003
INVENTOR(S)    : V.V Ramana, K.R. Yamuna and I. Jaunakais It is certified that error appears in the above-identified patent and that said Letters Patent is hereby corrected as shown below:

Title page,
Item [56], References Cited, OTHER PUBLICATIONS, after "Label, 1994", delete remainder of line, and insert at the beginning of the next line -- 2000 General Properties of Filter Papers, What --.
Item [57], ABSTRACT,
Lines 1 and 3, insert -- colorimetric -- for "calorimetric", each occurrence.

Column 1,
Lines 9, 22 and 63, insert -- colorimetric -- for "calorimetric", each occurrence.

Column 2,
Line 5, insert -- colorimetric -- for "calorimetric", each occurrence.

Column 3,
Line 47, insert -- colorimetric -- for "calorimetric", each occurrence.

Column 4,
Lines 24, 31, 33 and 39, insert -- colorimetric -- for "calorimetric", each occurrence.

Column 5,
Lines 31 and 35, insert -- colorimetric -- for "calorimetric", each occurrence.
Line 67, after "the" delete ".".

Column 7,
Line 58, insert -- colorimetric -- for "calorimetric", each occurrence.

UNITED STATES PATENT AND TRADEMARK OFFICE
CERTIFICATE OF CORRECTION

PATENT NO.    : 6,541,269 B1
DATED         : April 1, 2003
INVENTOR(S)   : V.V Ramana, K.R. Yamuna and I. Jaunakais It is certified that error appears in the above-identified patent and that said Letters Patent is hereby corrected as shown below:

<u>Column 8,</u>
Lines 57 and 59, for "calorimetric", each occurrence, insert -- colorimetric --.

<u>Column 10,</u>
Line 12, "positely" should read -- oppositely --.

Signed and Sealed this

Fifth Day of August, 2003

JAMES E. ROGAN
*Director of the United States Patent and Trademark Office*